United States Patent [19]

Spaltro et al.

[11] Patent Number: 5,202,111
[45] Date of Patent: Apr. 13, 1993

[54] PHOSPHORYLATED POLYHYDROXY COMPOUNDS FOR TARTAR CONTROL

[75] Inventors: Suree M. Spaltro, Denville, N.J.; Michael P. Aronson, West Nyack, N.Y.

[73] Assignee: Chesebrough-Pond's USA Co., Division of Conopco, Inc., Greenwich, Conn.

[21] Appl. No.: 697,835

[22] Filed: May 9, 1991

[51] Int. Cl.$^5$ .................... A61K 7/16; A61K 13/70
[52] U.S. Cl. .................... 424/49; 549/221; 558/186; 424/52
[58] Field of Search .................... 536/117; 549/221; 424/49-52; 558/186

[56] References Cited

U.S. PATENT DOCUMENTS

| | | | |
|---|---|---|---|
| 3,428,624 | 2/1969 | Toy | 424/49 |
| 3,437,652 | 4/1969 | Campbell et al. | 424/49 |
| 3,592,770 | 7/1971 | Lambiris | 424/49 |
| 3,666,855 | 5/1972 | Muhler | 514/105 |
| 3,881,000 | 4/1975 | Freidmann et al. | 514/105 |
| 4,193,988 | 3/1980 | Forward et al. | 424/52 |
| 4,283,335 | 8/1981 | Minn | 549/221 |
| 4,395,374 | 7/1983 | Dutra et al. | 549/221 |
| 4,483,705 | 11/1984 | Purdum | 549/221 |
| 4,606,912 | 8/1986 | Rudy et al. | 424/52 |
| 4,610,873 | 9/1986 | Rudy et al. | 424/52 |
| 4,612,191 | 9/1986 | Yeh et al. | 424/52 |
| 4,726,943 | 2/1988 | Klueppel et al. | 424/49 |
| 4,777,163 | 10/1988 | Bosies et al. | 549/221 |
| 4,786,740 | 11/1988 | Mirviss et al. | 549/221 |
| 4,826,675 | 5/1989 | Gaffar et al. | 424/52 |
| 4,853,476 | 8/1989 | Petrakis et al. | 549/221 |
| 4,867,989 | 9/1989 | Silva et al. | 424/48 |
| 4,892,724 | 1/1990 | Amjad | 424/49 |
| 4,933,475 | 6/1990 | Johnson et al. | 549/221 |
| 5,001,114 | 3/1991 | McDaniel | 536/117 |

FOREIGN PATENT DOCUMENTS 1009957 11/1965 United Kingdom .

*Primary Examiner*—Ronald W. Griffin
*Attorney, Agent, or Firm*—Milton L. Honig

[57] ABSTRACT

A composition and method for controlling tartar formation in the mouth is reported based upon phosphorylated polyhydroxy substances. These substances are formed by phosphorylation of a polyhydroxy starting compound of molecular weight no higher than 5000, have a molar substitution of at least 2 based on molecular weight of an average repeat unit in the starting polyhydroxy compound and possess phosphate ester linkages satisfying at least one criteria selected from:
(a) at least one multi-substituted phosphate ester linked through an oxygen atom to a single carbon of the polyhydroxy compound; and
(b) at least two monophosphate groups separated by no more than three carbon atoms.

12 Claims, No Drawings

PHOSPHORYLATED POLYHYDROXY COMPOUNDS FOR TARTAR CONTROL

BACKGROUND OF THE INVENTION

1. Field of the Invention

The invention relates to new antitartar agents, methods to prepare them, dentifice compositions containing these agents and use of such compositions to control tartar accumulation on teeth.

2. Related Art

A wide variety of materials are known that inhibit crystallization of hydroxyapatite to achieve reduced dental calculus or tartar. These compounds include simple inorganic polyphosphates, organophosphonates and various synthetic anionic polyelectrolytes.

The phosphate groups which are associated with a variety of naturally occurring salivary proteins are also known to bind tightly to enamel surfaces (hydroxyapatite). These have been implicated in the formation of pellicle. Saliva also contains phosphorylated peptides and proteins which act as potent crystal inhibitors. The active phosphate group on these materials is phosphoserine.

Much less research has been carried out on phosphorylated polyhydroxy compounds in conjunction with oral care. One of the earliest patents was British Patent 1,009,957 (Colonial Sugar Refining Co. Ltd.) which suggested derivatives of sugar phosphates for use as cariostatic agents. Related to this disclosure is U.S. Pat. No. 3,437,652 (Campbell et al.), U.S. Pat. No. 3,428,624 (Toy) and U.S. Pat. No. 3,592,770 (Lambris) each of which is also assigned to the Colonial Sugar Refining Co. Ltd. and discuss synthetic routes to phosphorylated carbohydrate derivatives. Improvements in anticaries effectiveness of glycerophosphates in combination with sodium monofluorophosphate were reported in U.S. Pat. No. 4,193,988 (Forward et al.). See also the background art of U.S. Pat. No. 4,726,943 (Klueppel et al.) that discloses fructose-6-phosphate, sorbitol-6-phosphate, glucose-1-phosphate and glucose-6-phosphate as having caries-prophylactic effects and minimal but insufficient activity in inhibiting crystal growth of apatite. Anticalculus compositions have been reported in U.S. Pat. No. 4,826,675 (Gaffar et al.) relating to phosphates of phytic acid.

Evident from the above-noted art is that phosphorylated polyhydroxy compounds have some benefit as anticariogenic agents but that antitartar activity of such materials is low to nonexistent.

Accordingly it is an object of the present invention to provide oral compositions of improved antitartar effectiveness.

A further object of the present invention is to provide antitartar agents having significant antitartar activity and being derived from relatively safe starting materials such as saccharides and polyols.

These and other objects of the present invention will become more apparent in light of the detailed description and examples which follow.

SUMMARY OF THE INVENTION

An oral composition is provided comprising:
(i) an anticaries agent present in an effective amount to reduce caries; and
(ii) an antitartar agent present in an effective amount to inhibit tartar formation, the agent being formed by phosphorylation of a polyhydroxy starting compound of molecular weight no higher than 5000, the phosphorylated polyhydroxy compound having a molar substitution of at least 2 based on molecular weight of an average repeat unit in the starting polyhydroxy compound and possessing phosphate ester linkages satisfying at least one criteria selected from the group consisting of:
(a) at least one multi-substituted phosphate ester linked through an oxygen atom to a single carbon of the polyhydroxy compound; and
(b) at least two monophosphate groups separated by no more than three carbon atoms.

A preferred method to prepare the aforementioned antitartar agents is also disclosed and comprises:
(i) forming a mixture of anhydrous phosphoric acid and orthophosphoric acid in a weight ratio of from about 5:1 to 1:5;
(ii) heating the mixture at a temperature to achieve a clear solution;
(iii) adding to the solution a polyhydroxy compound of molecular weight no higher than 5000 to form a phosphorylated product with at least molar substitution of 2 phosphates based on molecular weight of an average repeat unit in the polyhydroxy compound; and
(iv) neutralizing the product with an effective amount of a base to obtain a phosphate ester.

DETAILED DESCRIPTION

Now it has been found that certain types of phosphorylated polyhydric alcohols are very effective toward inhibiting the crystallization and growth of calcium phosphate under conditions found in the mouth. Compounds that are most effective as antitartar agents are those having a molar substitution of phosphate groups of at least 2 based on average molecular weight of repeat units in the starting polyhydroxy material. Furthermore, the arrangement of the phosphate groups is critical requiring the agent to possess phosphate ester linkages satisfying one or both of the following criteria:
(i) di, tri or higher phosphate esters attached through oxygen to a single carbon; and/or
(ii) two or more monophosphate groups which are separated by no more than three carbon atoms. The polyhydroxy compounds should also be water-soluble, have at least two hydroxyl groups per molecule or average repeat unit in the case of an oligomer and a molecular weight of between 50 and 5000, preferably between 100 to 2000 and most preferably between 100 and 500.

Illustrative of the polyhydroxy compounds serving as phosphorylation substrates are the acyclic polyols, cyclic polyols and higher oligosaccharides. Examples of acyclic polyols are glycerol, sorbitol, xylitol, citric acid and D-gluconic acid and its derivatives such as lactobionic acid. Examples of cyclic polyols are the mono-, di- and higher saccharides such as glucose, arabinose, fructose, galactose, maltose, sucrose, lactose, cellobiose, melezitose, raffinose and the cyclic uronic acids such as galacturonic acid. Higher oligosaccharides can be derived from dextran, starch, gums, cellulose and chitin; these oligosaccharides may be cyclic as in the case of dextrins or acyclic as in the case of maltodextran. Included in the higher oligosaccharide category are modified saccharides and polysaccharides such as alkylpolyglycosides. Preferred are polyhydroxy compounds derived from polysaccharides having from 1 to 15 saccharide units.

Phosphorylation of the polyhydroxy compounds can be controlled by careful selection of reaction conditions. According to the present invention these reaction conditions must be directed toward formation of the correct molar substitution of phosphate groups (>2 based on the molecular weight of the average repeat unit) and produce the correct arrangement of phosphate ester linkages, i.e. a preponderance of di, tri or higher phosphate esters attached to a single carbon atom and/or two or more monophosphate esters attached to the same molecule but separated by no more than 3 carbon atoms.

A variety of well-known techniques can be employed to prepare the phosphorylated alcohols of the present invention. These techniques have been reported in publications that include: U.S. Pat. No. 4,166,173 (Wurzburg et al.); "Phosphorylation in Organic Media" by Clarke et al., *J. Am. Chem. Soc.*, 88, 4401 (1966); Whistler et al., *Arch. Biochem. and Biophys.*, 135, 396 (1969); Sacco et al., *Carbohydrate Res.*, 184. 193 ( 1988); and Ferrel et al., *J. Am. Chem. Soc.*, 2101 (1948).

The most preferred route involves direct reaction of the polyol in anhydrous phosphoric acid. Reaction takes place at room temperature in a dry atmosphere. The amount of substitution and type of phosphate ester linkages can be manipulated by controlling reactant ratios. Another advantage of this reaction is that solvents are not required and there are minimum by-products. Absence of by-products is particularly advantageous in oral care products. It is well-known that phosphorylation of polyols designed to provide a high molar substitution yield a mixture of products. For the purposes of the present invention this is entirely acceptable provided the mixture contains a preponderance of species meeting the key structural elements described hereinabove (i.e. molar substitution and arrangement of phosphate groups).

Normally the phosphorylated compounds will be present in the compositions at concentrations f rom about 0.01 to about 10%, preferably from about 1 to 5% by weight of the total composition.

The phosphorylated compounds of the present invention can be incorporated into various types of oral care products. These products include toothpaste, gels, mouthwashes, lozenges, chewing gums, creams and powders. A variety of ingredients may be utilized to form such products. These ingredients include abrasives, thickening agents, sources of fluoride, adjunct anticalculus agents, antiplaque agents, surfactants, flavors and carriers.

When the oral compositions are in the form of a toothpaste or gel there will typically be included a natural or synthetic thickening agent in an amount from 0.1-10%, preferably about 0.5-5% by weight. Thickeners may include hydroxypropyl methyl cellulose, hydroxyethyl cellulose, sodium carboxymethyl cellulose, xanthan gum, tragacanth gum, karaya gum, arabic gum, Irish moss, starch, alginates, carrageenans and silicas. Synthetic thickening agents such as the crosslinked polyacrylate resins sold by Goodrich under the Carbopol trademark are also suitable. The amount of thickening agent will generally be between about 0.1 and 10% by weight.

Surfactants are normally also included in the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

When in the form of a toothpaste or gel, the oral compositions will normally include an abrasive. Abrasives may be selected from water-insoluble alkali or alkaline earth metal salts of metaphosphates, carbonates, bicarbonates, aluminates and silicates. Especially preferred are silicas, dicalcium phosphate and calcium carbonate. Amounts of the abrasive will range from about 5% to about 80% by weight.

Adjunct tartar control agents, especially inorganic compounds containing phosphorus, may be combined with the phosphorylated polyols of the present invention. Inorganic phosphorus adjuncts may include any of the water-soluble tripolyphosphates or pyrophosphates such as disodium and tetrasodium pyrophosphate, dipotassium and tetrapotassium pyrophosphate and mixtures thereof. Organic phosphorous compounds that may serve as adjuncts include polyphosphonates such as disodium ethane-1-hydroxy-1, 1-diphosphonate (EHDP), methanediphosphonic acid, and 2-phosphonobutane-1,2,4-tricarboxylic acid.

Other useful tartar control agents are metals such as zinc, various polycarboxylates such as low molecular weight polyacrylates and acrylate materials as taught in U.S. patent application Ser. No. 5,011,682 (Elliott et al).

Other ancillary agents such as phosphatase inhibitors and substantivity enhancers can be utilized. Copolymers of a polycarboxylate with hydrophobic monomers such as maleic anhydride/vinyl methyl ether (e.g. Gantrez ®) are particularly suitable for this application.

For anticaries protection, a source of fluoride ion will usually be present in the oral compositions. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anticaries agent will be present in an amount from about 0.05 to about 3% by weight, preferably 0.5 to 1% by weight. Other useful anticaries agents include sodium metaphosphate and hydroxyapatite.

Flavors that are usually present in the oral compositions are those based on oils of spearmint and peppermint. Examples of other flavoring materials include menthol, clove, wintergreen, eucalyptus and aniseed. Of course, many other flavors known in the art can also be employed. Flavors may range in concentration from 0.1 to 5% by weight.

Antiplaque agents may also be employed in compositions of the present invention. These may include zinc salts, copper salts, and antimicrobials such as chlorhexidenes and triclosan.

Carriers suitable for use with the polymers are preferably hydroxylic materials such as water, polyols and mixtures thereof. Polyols, sometimes referred to as humectants, include glycerol, sorbitol, propylene glycol, lactitol, xylitol, polypropylene glycol, polyethylene glycol, hydrogenated corn syrup and mixtures thereof. Particularly preferred as the carrier is a liquid mixture of 3-30% water, 0-80% glycerol and 20-80% sorbitol. Generally the amount of carrier will range from about 25 to 99.9% by weight, preferably from about 70 to 95% by weight.

Sweetening agents such as saccharin, sodium cyclamate, aspartame, sucrose and the like may be included at levels from about 0.1 to 5% by weight.

The following examples will more fully illustrate the embodiments of this invention. All parts, percentages and proportions referred to herein and in the appended claims are by weight of the total composition unless otherwise stated.

EXAMPLE 1

Phosphorylation of Polyhydroxy Compounds in an Aqueous System

Procedure A

The phosphorylating reagent was prepared by adding sodium tripolyphosphate (64.7g) with stirring to 100 ml of water in portions. The mixture was maintained below 37° C. and the mixture pH was adjusted to between 4.2 to 4.8 with orthophosphoric acid. This reagent (20 ml, 0.0186 moles) was heated to 70° C. Dextran (3 g, 0.017 moles of monomer, ex Polyscience Corp.) was added to portions thereof with vigorous stirring to give a viscous mixture. The mixture was heated to 105° C. for 5 hours and cooled to room temperature, it was poured into a large excess of isopropanol. Saturated sodium chloride solution was added to aid in polymer precipitation. The supernatant was discarded and the residue was dissolved in 20 ml water forming a crude polymer solution. Purification of this solution was achieved by ultrafiltration through a membrane of the appropriate molecular weight cutoff until the filtrate gave a FTIR spectrum of water. The retentate was lyophilized to give a white powder.

This procedure typically produces -phosphorylated compounds containing a low monomer substitution and only monophosphate ester. Examples of compounds made using this method are dextran of molecular weight around 15,000 with a monomer substitution of 0.007 and 0.014, respectively. These compounds do not inhibit crystal growth according to the PCIR assay.

EXAMPLE 2

Phosphorylation of Polyhydroxy Compounds in Organic Media

Procedure B

Polyphosphoric acid (0.01 moles) was added to a flask under dry, inert atmosphere. Tri-N-butylamine (0.0374 moles) and 20 ml of dry N,N-dimethylformamide were added to the acid and the mixture was heated to about 80° C. with stirring. Dextran (0.0036 moles of monomer, ex Polyscience Corp.) was added to the hot mixture and heating was continued. The mixture was maintained at a temperature of 120° C. for six hours and then allowed to cool to room temperature. Thereafter, the mixture was poured into a large excess of ethanol followed by addition of saturated sodium chloride solution to facilitate polymer precipitation. The precipitate was collected, dissolved in water and the resultant crude polymer solution was pH adjusted to between 9 and 10. Liberated amine was evaporated off under reduced pressure. Purification of the polymer solution was accomplished through ultrafiltration using water, 1M sodium chloride solution and then again, water. Finally, the concentrated, purified polymer solution was lyophilized.

This method was practiced with dextrans of different molecular weights (15,000 and 6,000) and hydroxyethylcellulose (MW 27,000) to provide a monomer substitution ranging from 0.04 to 2.5. Phosphorus-31 NMR of these materials revealed the presence of both mono- and di-phosphate esters. Yet, even highly substituted polymers with the correct arrangement of the phosphate groups displayed no crystal growth inhibition because the molecular weight was outside the required range.

When the procedure was repeated with melezitose, a trisaccharide, the resultant product contained mono-, di-, tri- and higher phosphate esters with an average of two phosphate groups per monomer unit. PCIR assay (Example 7) indicated the product to be extremely effective in inhibiting crystal growth even at a low level of 0.01%.

EXAMPLE 3

Phosphorylation of Alkylpolyglycosides in Organic Media

Procedure C

This procedure is especially suitable for polyols that possess hydrophobic functionalities.

An alkylpolyglycoside (1 mole, MW 410, ex Horizon Chemical Co.) was dissolved in 1200 ml of dry tetrahydrofuran under a dry, inert atmosphere. The phosphorylating reagent was prepared by adding 2 moles of phosphorus pentoxide to 2 moles of orthophosphoric acid. With vigorous stirring, the reagent was added to the alkylpolyglycoside solution to form a smooth suspension. The mixture was heated to refluxing for 6 hours and allowed to cool to room temperature before being neutralized with a concentrated solution of potassium hydroxide. Any remaining solvent was evaporated off under reduced pressure to give a viscous mixture which was then dialyzed sequentially against distilled water, 1M sodium chloride solution and distilled water until the conductivity of the dialyzate was that of water. Retentate was pooled and lyophilized.

A product obtained from this procedure gave a monomer substitution of 4 and displayed good crystal growth inhibition.

EXAMPLE 4

Phosphorylation in Anhydrous Phosphoric Acid

Procedure D

This is a preferred method for preparing phosphorylated polyols for dental care applications.

Anhydrous phosphoric acid was prepared by adding 30 g of phosphorus pentoxide to 40 g of 85% orthophosphoric acid. The mixture was heated with mixing to give a clear solution. Polyhydroxy compound (7 g) was then added to the phosphoric acid with thorough agitation followed by maintenance at room temperature in a dry atmosphere for a specified period. At the end of the reaction, the mixture was diluted by adding it to crushed ice. The diluted solution was neutralized with 10N potassium hydroxide to pH 7–8. The mixture was purified via dialysis as in Example 3.

Procedure D was applied to a range of polyols including galactose, glucose, melibiose, maltose, raffinose, melezitose, sorbitol and xylitol. A sample phosphorylated melibiose gave about 45% of the diphosphate ester and about 55% of the monophosphate ester. These results were typical of materials prepared using this procedure.

EXAMPLE 5

Characterization of Phosohorylated Compounds

Degree of Monomer Substitution

Determination of the number of monomer units was performed by the orcinol method (Winzler, R.J., in Methods of Biochemical Analysis, Vol. II, p. 290, 1955) using the particular starting material to generate the standard plot. Generally a series of the test compound solutions were treated with freshly prepared acidic orcinol reagent and heated to give a particular color with maximum absorbance at 540 nm.

Determination of phosphorus concentration was carried out using the Chen's method (Chen, P.S., Toribara, T.Y. and Warner, H., Anal. Chem., 28, 1756, 1956). A standard plot was generated using the highest purity potassium dihydrogen phosphate. This procedure involved the use of acidic molydate reagent which when heated with free phosphate gave a color complex which absorbs at 820 nm. Phosphorylated compounds were generally degraded to free phosphates by acid digestion first with sulfuric acid then with perchloric acid.

These two analyses gave a ratio of the phosphate moiety to the monomer unit which was defined as the degree of monomer substitution. Other characterization techniques employed were: FTIR, proton, carbon-13 and phosphorus-31 NMR, and GPC.

EXAMPLE 6

Method of Preparation

This example illustrates the importance of selecting proper reactant ratios in the synthesis to achieve products with the desired chemical and physical properties. In turn, these properties influence the effectiveness of crystal growth inhibition.

Raffinose, a typical trisaccharide, was phosphorylated by varying the molar ratio from 2.6:1 to 8.0:1 of the anhydrous phosphoric acid to the available hydroxyl groups in the molecule. Molar ratios of 3.0 to 4.0:1 were found most suitable and gave the desired products. For acyclic polyols, a lower molar ratio of 2.0 to 3.0:1 was most effective.

TABLE I

| | Effect of Reactant Ratios | |
|---|---|---|
| Saccharide | Mole Phosphoric Acid To Mole Hydroxyl Groups | Monomer Substitution |
| Raffinose | 8:1 | 1.04 |
| | 3.9:1 | 2.9 |
| | 2.6:1 | 2.3 |

EXAMPLE 7

Crystal Growth Inhibition Assay

The PCIR (Potential Calculus Inhibition Ratio) method assays the ability of an agent to bind hydroxyapatite crystals thereby preventing seeds from initiating calcium depletion from a metastable calcifying solution.

This assay involved the treatment of synthetic hydroxyapatite with a potential anticalculus agent followed by incubation of the treated hydroxyapatite with a metastable calcium-phosphate solution at 37° C. Samples were filtered to remove crystals of calcium phosphate formed during the incubation and free calcium in the filtrate was measured using an EDTA-magnesium back titration method. An autotitrator was used to determine the colorimetric change that occurred during the titration procedure. A Potential Calculus Inhibition Ratio (PCIR) was calculated for each test sample based on one hour crystal growth. The ratio was determined as the difference between calcium depletion of control and of a sample divided by the calcium depletion of the control. The higher the PCIR value, the greater the prevention of crystal growth which, in turn, indicates good potential for anticalculus activity.

EXAMPLE 8

A series of comparative experiments were conducted using the Potential Crystal Growth Inhibition Ratio (PCIR) assay (Example 7). These tests were conducted to compare monophosphate ester salts such as glucose-6-phosphate relative to those of the present invention characterized by a higher degree of phosphorylation with mono-, di-, tri- and higher phosphate ester linkages and the appropriate geometrical arrangement of the phosphate functionalities. Table II lists the results of these experiments.

TABLE II

| Adduct | Monomer Substitution | Conc. | PCIR |
|---|---|---|---|
| Commercially available materials: | | | |
| Glucose-6-phosphate | 1.0 | 0.1% | 0.03 |
| Glucose-1,6-diphosphate | 2.0 | 0.1% | 0.14 |
| | | 0.01% | 0.13 |
| Fructose-1,6-diphosphate | 2.0 | 0.1% | 0.12 |
| | | 0.1% | 0.11 |
| Adenosine diphosphate | 2.0 | 0.1% | 0.20 |
| | | 0.01% | 0.17 |
| Phosphorylated Monosaccharides: | | | |
| D-galactose | 2.2 | 0.1% | 0.92 |
| | | 0.01% | 0.69 |
| D-galactose | 2.7 | 0.1% | 0.93 |
| | | 0.01% | 0.51 |
| D-glucose | 5.0 | 0.1% | 0.98 |
| | | 0.01% | 0.74 |
| Phosphorylated Disaccharides: | | | |
| Lactose | 5.1 | 0.1% | 0.88 |
| | | 0.01% | 0.49 |
| Maltose | 3.5 | 0.1% | 0.92 |
| | | 0.01% | 0.63 |
| Melibiose | 3.7 | 0.1% | 0.88 |
| | | 0.01% | 0.70 |
| Phosphorylated Trisaccharides: | | | |
| Melezitose | 2.5 | 0.1% | 0.81 |
| | | 0.01% | 0.83 |
| Raffinose | 2.3 | 0.1% | 0.76 |
| | | 0.01% | 0.11 |
| Phosphorylated Acyclic Compounds: | | | |
| Xylitol | 4.7 | 0.3% | 0.81 |
| Sorbitol | 4.2 | 1.0% | 0.88 |
| Phosphorylated Modified Saccharides: | | | |
| Alkylpolyglycoside | 4.1 | 0.1% | 0.82 |
| | | 0.01% | 0.16 |
| Phosphorylated Polysaccharide: | | | |
| Dextran | 1.7 | 0.5% | 0.19 |
| | 0.014 | 1.0% | 0.22 |

Based on the above results, it is evident that discreet monophosphate esters such as glucose-6-phosphate have essentially no antitartar activity. Even at a monomer substitution of 2, the discreet monophosphate esters provided low efficacy. Compounds containing a pyrophosphate ester linkage such as adenosine diphosphate (not a polyol phosphate) gave an increased but still low efficacy. By contrast, the compounds claimed for the present invention provided significant activity. The activity is a result of the correct degree of phosphorylation, the correct geometrical arrangement of the phosphate groups and the overall molecular weights which combine to give the proper chemical and physical properties.

EXAMPLE 9

A typical toothpaste formulation is hereunder illustrated incorporating the antitartar compounds of the present invention.

| Ingredient | Percentage |
| --- | --- |
| Sorbitol and other polyols (70% syrup) | 56.3 |
| Silica Xerogel | 14.0 |
| Silica Aerogel | 10.0 |
| Polyethylene Glycol | 5.0 |
| Sodium Lauryl Sulfate | 1.6 |
| Flavor | 1.10 |
| Phosphorylated Actives | 1–3 |
| Sodium Monofluorophosphate | 0.8 |
| Sodium Carboxymethylcellulose | 0.4 |
| Sodium Saccharin | 0.2 |
| Water | to 100% |
| Colorant (1% solution) | 0.07 |

EXAMPLE 10

A typical mint-type mouthwash is hereunder illustrated incorporating the antitartar actives of the present invention.

| Ingredient | Percentage |
| --- | --- |
| Phosphorylated Actives | 1–3.5 |
| Ethyl alcohol | 10.0 |
| Flavor (methol 30%, methyl salicylate 30%, peppermint oil 30%, eucalyptol 10%) | 0.25 |
| Glycerin | 7.50 |
| Polyoxyethylene/polyoxypropylene block polymer (Polaxamer 407) | 2.0 |
| Sodium Saccharin | 0.05 |
| Water | to 100% |

Although this invention has been described with reference to specific examples, it will be apparent to one skilled in the art that various modifications may be made thereto which fall within the scope and purview of the invention.

What is claimed:

1. An antitartar oral composition comprising:
   (i) an anticaries agent present in an effective amount to reduce caries; and
   (ii) an antitartar agent present in an effective amount to inhibit tartar accumulation, said agent being formed by phosphorylation of a polyhydroxy starting compound of molecular weight no higher than 5000, the phosphorylated polyhydroxy compound having a molar substitution of at least 2 based on molecular weight of an average repeat unit in the starting polyhydroxy compound and possessing phosphate ester linkages satisfying at least one criteria selected from the group consisting of:
   (a) at least one multi-substituted phosphate ester linked through an oxygen atom to a single carbon of the polyhydroxy compound; and
   (b) at least two monophosphate groups separated by no more than three carbon atoms.

2. A composition according to claim 1 wherein the polyhydroxy compound is selected from the group consisting of acyclic polyols, cyclic polyols, higher oligosaccharides and mixtures thereof.

3. A composition according to claim 2 wherein the acyclic polyols are selected from the group consisting of glycerol, sorbitol, xylitol, citric acid, D-gluconic acid, lactobionic acid and derivatives thereof.

4. A composition according to claim 2 wherein the cyclic polyols are selected from the group consisting of glucose, arabinose, fructose, galactose, maltose, sucrose, lactose, melibiose, cellobiose, melezitose, raffinose, uronic acids and alkylpolyglycosides.

5. A composition according to claim 2 wherein the oligosaccharides are selected from the group consisting of dextran, starch, gums, cellulose and chitin.

6. A composition according to claim 1 wherein the anticaries agent is a fluoride present in an amount ranging from about 0.05 to about 3% by weight.

7. A composition according to claim 1 wherein the amount of the antitartar agent ranges from about 0.01 to about 10% by weight.

8. A composition according to claim 1 further comprising a dental abrasive in an amount from about 5% to about 80% by weight.

9. A method of controlling dental tartar which comprises treating teeth with a composition according to claim 1.

10. A method according to claim 9 wherein the composition is applied in the form of an aqueous mouth rinse.

11. A method according to claim 9 wherein the composition is incorporated into a dental paste and brushed onto the teeth.

12. A process for preparing a phosphate ester comprising:
   (i) forming a mixture of anhydrous phosphoric acid and orthophosphoric acid in a weight ratio of from about 5:1 to 1:5;
   (ii) heating said mixture at a temperature to achieve a clear solution;
   (iii) adding to said solution a polyhydroxy compound of molecular weight no higher than 5000 to form a phosphorylated product with at least molar substitution of 2 phosphates based on molecular weight of an average repeat unit in said polyhydroxy compound; and
   (iv) neutralizing said product with an effective amount of a base to obtain said phosphate ester.

* * * * *